United States Patent
Feng et al.

(10) Patent No.: US 12,110,538 B2
(45) Date of Patent: Oct. 8, 2024

(54) METHOD FOR DETECTING NUCLEIC ACID BASED ON PROKARYOTIC ARGONAUTE PROTEIN AND APPLICATION THEREOF

(71) Applicant: Jiaohong Biotechnology (Shanghai) Co., Ltd., Shanghai (CN)

(72) Inventors: Yan Feng, Shanghai (CN); Guanhua Xun, Shanghai (CN); Qian Liu, Shanghai (CN); Yuesheng Chong, Shanghai (CN)

(73) Assignee: Jiaohong Biotechnology (Shanghai) Co., Ltd., Shanghai (CN)

( * ) Notice: Subject to any disclaimer, the term of this patent is extended or adjusted under 35 U.S.C. 154(b) by 1039 days.

(21) Appl. No.: 17/045,393

(22) PCT Filed: Oct. 12, 2018

(86) PCT No.: PCT/CN2018/110056
§ 371 (c)(1),
(2) Date: Oct. 5, 2020

(87) PCT Pub. No.: WO2019/192156
PCT Pub. Date: Oct. 10, 2019

(65) Prior Publication Data
US 2021/0164024 A1 Jun. 3, 2021

(30) Foreign Application Priority Data
Apr. 3, 2018 (CN) .......................... 201810291873.0

(51) Int. Cl.
*C12Q 1/70* (2006.01)
*C12Q 1/6818* (2018.01)

(52) U.S. Cl.
CPC .......... *C12Q 1/6818* (2013.01); *C12Q 1/708* (2013.01)

(58) Field of Classification Search
None
See application file for complete search history.

(56) References Cited

U.S. PATENT DOCUMENTS 10,253,311 B2 * 4/2019 Doudna ................. C12P 19/34

FOREIGN PATENT DOCUMENTS

| CN | 107805634 A | 3/2018 |
| WO | 2016196887 A1 | 12/2016 |

OTHER PUBLICATIONS

Wierer et al. (PLOS ONE, p. 1-19, May 2016).*
Enghiad et al. (Synthetic Biology, 2017, p. 752-757).*

* cited by examiner

*Primary Examiner* — Agnieszka Boesen
(74) *Attorney, Agent, or Firm* — NKL Law; Allen Xue

(57) ABSTRACT

Provided are a method for detecting a nucleic acid based on prokaryotic Argonaute protein and an application thereof. In particular, provided is a system for detecting a target nucleic acid molecule. The system comprises guide ssDNA, a gene-editing enzyme *Pyrococcus furiosus* Argonaute (PfAgo), and a fluorescent reporter nucleic acid.

14 Claims, 18 Drawing Sheets
Specification includes a Sequence Listing.

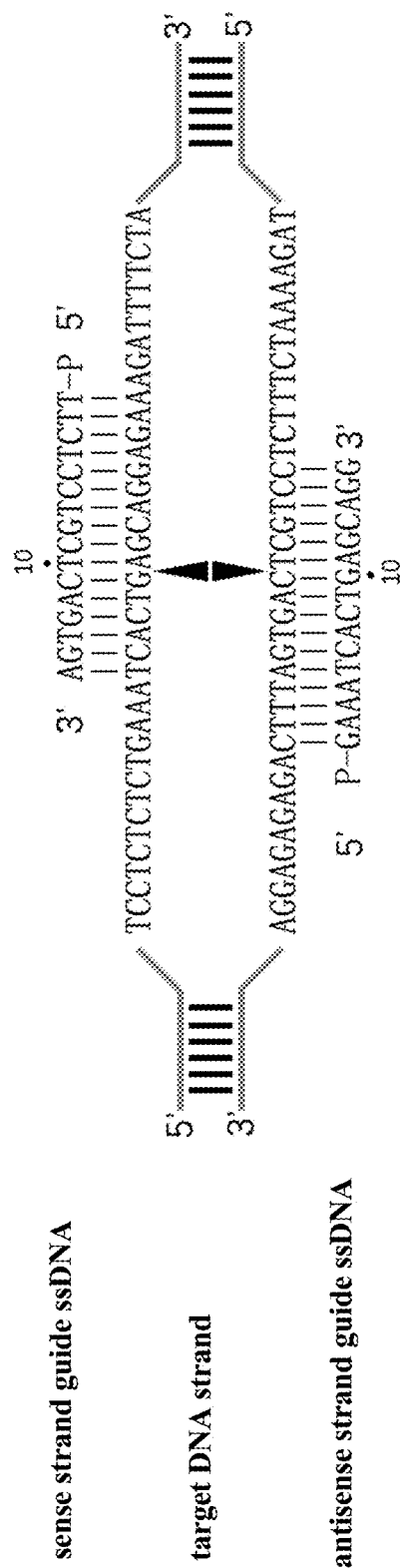

SEQUENCE LISTING

<160> NUMBER OF SEQ ID NOS: 22

<210> SEQ ID NO 1
<211> LENGTH: 95
<212> TYPE: DNA
<213> ORGANISM: Artificial Sequence
<220> FEATURE:
<223> OTHER INFORMATION: synthesized

<400> SEQUENCE: 1
ctgtgactcc atagaaaatc tttctcctgc tcagtgattt cagagagagg atctcgtgta    60
gaaattgctt tgagctgttc tttgtcattt tccct                              95

<210> SEQ ID NO 2
<211> LENGTH: 27
<212> TYPE: DNA
<213> ORGANISM: Artificial Sequence
<220> FEATURE:
<223> OTHER INFORMATION: synthesized

<400> SEQUENCE: 2
ctgtgactcc atagaaaatc tttctcc                                       27

<210> SEQ ID NO 3
<211> LENGTH: 24
<212> TYPE: DNA
<213> ORGANISM: Artificial Sequence
<220> FEATURE:
<223> OTHER INFORMATION: synthesized

<400> SEQUENCE: 3
agggaaaatg acaaagaaca gctc                                          24

<210> SEQ ID NO 4
<211> LENGTH: 16
<212> TYPE: DNA
<213> ORGANISM: Artificial Sequence
<220> FEATURE:
<223> OTHER INFORMATION: synthesized

<400> SEQUENCE: 4
ttctcctgct cagtga                                                   16

<210> SEQ ID NO 5
<211> LENGTH: 16
<212> TYPE: DNA
<213> ORGANISM: Artificial Sequence
<220> FEATURE:
<223> OTHER INFORMATION: synthesized

<400> SEQUENCE: 5
tgaaatcact gagcag                                                   16

<210> SEQ ID NO 6
<211> LENGTH: 17
<212> TYPE: DNA
<213> ORGANISM: Artificial Sequence
<220> FEATURE:
<223> OTHER INFORMATION: synthesized

<400> SEQUENCE: 6
ctcgtcctct ttctaaa                                                  17

<210> SEQ ID NO 7
<211> LENGTH: 22

```
<212> TYPE: DNA
<213> ORGANISM: Artificial Sequence
<220> FEATURE:
<223> OTHER INFORMATION: synthesized

<400> SEQUENCE: 7
ccggtgagta caccggaatt gc                                              22

<210> SEQ ID NO 8
<211> LENGTH: 16
<212> TYPE: DNA
<213> ORGANISM: Artificial Sequence
<220> FEATURE:
<223> OTHER INFORMATION: synthesized

<400> SEQUENCE: 8
gcagtcttgc gggggc                                                     16

<210> SEQ ID NO 9
<211> LENGTH: 16
<212> TYPE: DNA
<213> ORGANISM: Artificial Sequence
<220> FEATURE:
<223> OTHER INFORMATION: synthesized

<400> SEQUENCE: 9
tgcccaaatc tccagg                                                     16

<210> SEQ ID NO 10
<211> LENGTH: 16
<212> TYPE: DNA
<213> ORGANISM: Artificial Sequence
<220> FEATURE:
<223> OTHER INFORMATION: synthesized

<400> SEQUENCE: 10
tatgcctgga gatttg                                                     16

<210> SEQ ID NO 11
<211> LENGTH: 30
<212> TYPE: DNA
<213> ORGANISM: Artificial Sequence
<220> FEATURE:
<223> OTHER INFORMATION: synthesized

<400> SEQUENCE: 11
agtctcgcgg gggcacgccc aaatctccag                                      30

<210> SEQ ID NO 12
<211> LENGTH: 22
<212> TYPE: DNA
<213> ORGANISM: Artificial Sequence
<220> FEATURE:
<223> OTHER INFORMATION: synthesized

<400> SEQUENCE: 12
ccggtgagta caccggaatt gc                                              22

<210> SEQ ID NO 13
<211> LENGTH: 16
<212> TYPE: DNA
<213> ORGANISM: Artificial Sequence
<220> FEATURE:
<223> OTHER INFORMATION: synthesized

<400> SEQUENCE: 13
```
gcagtcttgc gggggc                                               16

<210> SEQ ID NO 14
<211> LENGTH: 16
<212> TYPE: DNA
<213> ORGANISM: Artificial Sequence
<220> FEATURE:
<223> OTHER INFORMATION: synthesized

<400> SEQUENCE: 14
tgcccaaatg gccggg                                               16

<210> SEQ ID NO 15
<211> LENGTH: 16
<212> TYPE: DNA
<213> ORGANISM: Artificial Sequence
<220> FEATURE:
<223> OTHER INFORMATION: synthesized

<400> SEQUENCE: 15
tatgcccggc catttg                                               16

<210> SEQ ID NO 16
<211> LENGTH: 30
<212> TYPE: DNA
<213> ORGANISM: Artificial Sequence
<220> FEATURE:
<223> OTHER INFORMATION: synthesized

<400> SEQUENCE: 16
tggataaacc cactgtatgc ccggccattt                                30

<210> SEQ ID NO 17
<211> LENGTH: 31
<212> TYPE: DNA
<213> ORGANISM: Artificial Sequence
<220> FEATURE:
<223> OTHER INFORMATION: synthesized

<400> SEQUENCE: 17
cyacwcgcag tacmaaywtr wcahtatgtg c                              31

<210> SEQ ID NO 18
<211> LENGTH: 30
<212> TYPE: DNA
<213> ORGANISM: Artificial Sequence
<220> FEATURE:
<223> OTHER INFORMATION: synthesized

<400> SEQUENCE: 18
ttgaaaaata aaytgyaaat cawaytcytc                                30

<210> SEQ ID NO 19
<211> LENGTH: 16
<212> TYPE: DNA
<213> ORGANISM: Artificial Sequence
<220> FEATURE:
<223> OTHER INFORMATION: synthesized

<400> SEQUENCE: 19
ttgtatgtgc aagatg                                               16

<210> SEQ ID NO 20
<211> LENGTH: 16
<212> TYPE: DNA
<213> ORGANISM: Artificial Sequence

```
<220> FEATURE:
<223> OTHER INFORMATION: synthesized

<400> SEQUENCE: 20
ttgtatgtac cagatt                                                   16

<210> SEQ ID NO 21
<211> LENGTH: 16
<212> TYPE: DNA
<213> ORGANISM: Artificial Sequence
<220> FEATURE:
<223> OTHER INFORMATION: synthesized

<400> SEQUENCE: 21
tggagtacca acgaca                                                   16

<210> SEQ ID NO 22
<211> LENGTH: 16
<212> TYPE: DNA
<213> ORGANISM: Artificial Sequence
<220> FEATURE:
<223> OTHER INFORMATION: synthesized

<400> SEQUENCE: 22
tgcagtatag cagaca                                                   16
```

METHOD FOR DETECTING NUCLEIC ACID BASED ON PROKARYOTIC ARGONAUTE PROTEIN AND APPLICATION THEREOF

INCORPORATION OF SEQUENCE LISTING

This application contains a sequence listing submitted in Computer Readable Form (CRF). The CFR file containing the sequence listing entitled "PB4084187_ST25.txt", which was created on Oct. 5, 2020, and is 4,471 bytes in size. The information in the sequence listing is incorporated herein by reference in its entirety.

TECHNICAL FIELD

The present invention is in the field of biotechnology, and in particular relates to a method for detecting nucleic acid based on prokaryotic Argonaute protein and application thereof.

BACKGROUND

Nucleic acid detection technology is widely used in many fields such as molecular medical diagnosis, food safety inspection and environmental monitoring. Rapid, cheap and sensitive nucleic acid detection can be widely used in pathogen detection, genotyping, and disease course monitoring.

Although some traditional nucleic acid detection methods (qPCR, sequencing, southern blot, etc.) have been widely used, there are still some disadvantages. For example, qPCR and high-throughput sequencing have shortcomings such as time-consuming, with high cost and with complex design principles. In addition, for the extremely small quantity of nucleic acids to be detected, there is still a lack of satisfactory detection methods in the art.

At present, nucleic acid detection methods using gene editing enzymes include the methods using C2C2 enzyme-mediated collateral cleavage effect to detect target RNA. However, there is still a lack of methods for rapid and effective detection of target DNA (especially trace DNA).

Therefore, there is an urgent need in this field to develop nucleic acid detection methods with high sensitivity, good specificity, and high throughput for target DNA.

SUMMARY OF THE INVENTION

The purpose of the present invention is to provide a method based on nucleic acid detection with high sensitivity, good specificity and high throughput to target DNA, and the application thereof.

In a first aspect of the present invention, it provides a detection system for detecting target nucleic acid molecules, wherein the system comprises:
(a) a guide ssDNA pair;
(b) a gene editing enzyme *Pyrococcus furiosus* (Pf Ago); and
(c) a fluorescent reporter nucleic acid, which has a fluorescent group and a quenching group;
wherein the target nucleic acid molecule is target DNA.

In another preferred embodiment, the guide ssDNA pair includes a sense strand guide ssDNA and an antisense strand guide ssDNA.

In another preferred embodiment, the guide ssDNA is a 5'-phosphorylated single-stranded DNA molecule.

In another preferred embodiment, the guide ssDNA has a length of n bases, and n≥14.

In another preferred embodiment, n≤100, preferably ≤80, more preferably ≤60.

In another preferred embodiment, the length of the guide ssDNA is 14-60 nt, preferably 16-40 nt.

In another preferred embodiment, the number of the guide ssDNAs is one or more pairs.

In another preferred embodiment, the PfAgo enzyme is derived from the archaea *Pyrococcus furiosus*.

In another preferred embodiment, the PfAgo includes wild type PfAgo and mutant PfAgo.

In another preferred embodiment, the mutation sites corresponding to different types of the target nucleic acid molecules are at positions 10 and 11 of the guide ssDNA.

In another preferred embodiment, the detection system further comprises (d) a buffer.

In another preferred embodiment, the detection system further comprises primers for amplifying the target nucleic acid molecules.

In another preferred embodiment, the detection system further comprises the target nucleic acid molecules to be detected.

In another preferred embodiment, the target nucleic acid molecules (or the amplification product thereof) are cleaved by the PfAgo enzyme to produce a secondary guide ssDNA.

In another preferred embodiment, the sequences of the secondary guide ssDNA and the fluorescent reporter nucleic acid are complementary.

In another preferred embodiment, after the sequence complementary binding of the secondary guide ssDNA and the fluorescent reporter nucleic acid, the PfAgo enzyme is guided to cleave the fluorescent reporter nucleic acid, thereby generating a detectable signal (such as fluorescence).

In another preferred embodiment, the concentration of the target nucleic acid molecules to be detected in the detection system is 1-1000 copies/microliter or $10^3$-$10^{10}$ copies/microliter, preferably 100-1000 copies/microliter, more preferably 1-100 copies/microliter.

In another preferred embodiment, the concentration of the target nucleic acid molecules to be detected in the detection system is 1 fM-200 pM, preferably 1-1000 fM, more preferably 1-100 fM, and most preferably 1-20 fM.

In another preferred embodiment, the working temperature of the gene editing enzyme is 87-99° C.

In another preferred embodiment, in the detection system, the concentration of the fluorescent reporter nucleic acid is 100-1000 nM.

In another preferred embodiment, in the detection system, the molar ratio of the fluorescent reporter nucleic acid to the target nucleic acid molecules is $10^3$:1 to $10^8$:1, preferably $10^4$:1 to $10^7$:1.

In another preferred embodiment, the target DNA comprises cDNA.

In another preferred embodiment, the target DNA is selected from the group consisting of: single-stranded DNA (including cDNA), double-stranded DNA, and a combination thereof.

In another preferred embodiment, the fluorescent group and the quenching group are independently located at the 5' end and the 3' end of the fluorescent reporter nucleic acid.

In another preferred embodiment, the length of the fluorescent reporter nucleic acid is 9-100 nt, preferably 10-60 nt, more preferably 15-40 nt.

In another preferred embodiment, the target nucleic acid molecules comprise target nucleic acid molecules derived from a species selected from the group consisting of: a plant, an animal, a microorganism, a virus, and a combination thereof.

In another preferred embodiment, the target DNA is a synthetic or a naturally occurring DNA.

In another preferred embodiment, the target DNA comprises a wild-type or a mutant DNA.

In a second aspect of the invention, it provides a kit for detecting target nucleic acid molecules, comprising:
(i) the detection system according to the first aspect of the present invention or reagents used for the preparation of the detection system; and
(ii) instructions for use, which describe the method for detecting target nucleic acid molecules with the detection system.

In another preferred embodiment, the kit may further comprises a buffer.

In another preferred embodiment, the kit comprises:
(a) a first container and a guide ssDNA located in the first container;
(b) a second container and enzyme Pyrococcus furiosus Argonaute (PfAgo) located in the second container; and
(c) a third container and a fluorescent reporter nucleic acid located in the third container.

In another preferred embodiment, the kit further comprises:
(d) a fourth container and a buffer for enzyme digestion located in the fourth container.

In another preferred embodiment, the buffer for enzyme digestion comprises $MnCl_2$.

In another preferred embodiment, the kit further comprises:
(f) a fifth container and a primer or a primer pair for amplifying target nucleic acid molecules located in the fifth container;
(g) an optional sixth container and a polymerase for amplification reaction located in the sixth container; and
(h) an optional seventh container and an amplification buffer for amplification reaction located in the seventh container.

In a third aspect of the invention, it provides a method for detecting the presence or absence of target nucleic acid molecules in a sample, comprising the steps of:
(a) providing the detection system for detecting target nucleic acid molecules according to the first aspect of the present invention; and
(b) reacting the detection system with the sample to be tested at a certain temperature, to form a first reaction solution;
(c) performing a fluorescence detection on the first reaction solution, to obtain a fluorescence signal value;
wherein, if the fluorescence signal value is detected in the first reaction solution, it indicates that there is target nucleic acid molecules in the sample; and if the fluorescence signal value is not detected in the first reaction solution, it indicates that there is no target nucleic acid molecule in the sample.

In another preferred embodiment, the sample to be detected comprises an unamplified sample and an amplified (or nucleic acid amplified) sample.

In another preferred embodiment, the sample to be detected is a sample obtained by amplification.

In another preferred embodiment, the nucleic acid amplification method is selected from the group consisting of: PCR amplification, LAMP amplification, RPA amplification, ligase chain reaction, branched DNA amplification, NASBA, SDA, transcription-mediated amplification and rolling circle amplification.

In another preferred embodiment, the PCR comprises high temperature PCR, normal temperature PCR, and low temperature PCR.

In another preferred embodiment, the method is for detecting whether there is an SNP, a point mutation, a deletion, and/or an insertion for nucleic acids at a target site.

In another preferred embodiment, in the step (b), a microplate reader or a fluorescence spectrophotometer is used in the fluorescence detection.

In another preferred embodiment, the method is an in vitro method.

In another preferred embodiment, the method is non-diagnostic and non-therapeutic.

In a fourth aspect of the present invention, it provides use of the nuclease Pyrococcus furiosus Argonaute for preparing reagents or kits for detecting target nucleic acid molecules based on secondary cleavage.

In another preferred embodiment, the enzyme Pyrococcus furiosus Argonaute is derived from the archaea Pyrococcus furiosus; or the homologous analogue thereof with the same or similar functions.

In another preferred embodiment, the PfAgo includes wild type PfAgo and mutant PfAgo.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

DESCRIPTION OF THE FIGURES

FIG. 1 is a schematic diagram showing the first cleavage of the gene-encoding enzyme of the present invention, in which a pair of guide ssDNAs is designed for the same DNA strand, and the corresponding cleavage sites are marked by black arrows, and a blunt end is formed after the action of pfAgo enzyme.

FIG. 2 is a schematic diagram showing the second cleavage of the gene-encoding enzyme of the present invention, in which the specific cleavage guided by the primary guide ssDNAs produces the secondary guide ssDNAs.

DETAILED DESCRIPTION

Figure 3:
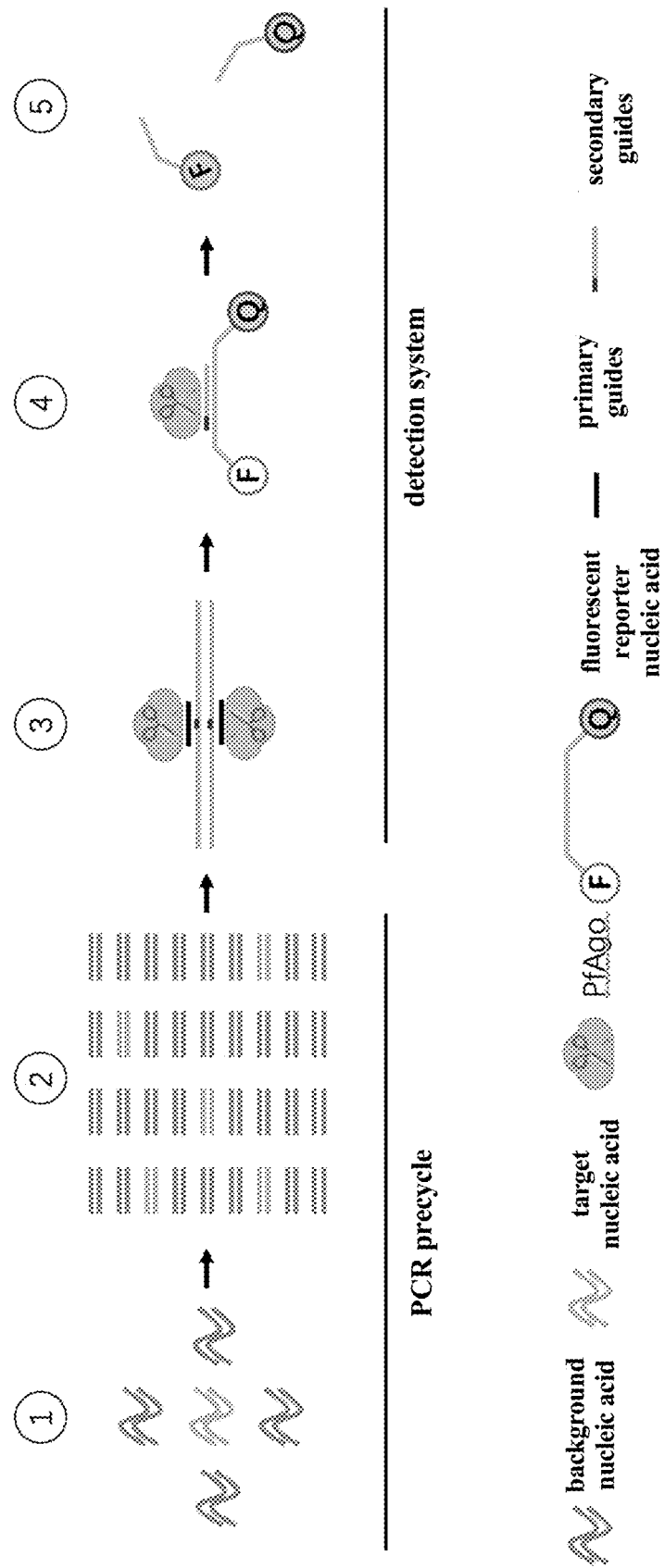
FIG. 3 shows the steps and principles of the detection method of the present invention.

By extensively and intensively studies, the present inventors have for the first time developed a nucleic acid detection method for target DNA with low detection limit, high sensitivity, simple operation, low detection cost, short time, and high throughput. The method of the present invention utilizes the characteristics of the PfpAgo enzyme, that is, after the first cleavage mediated by the primary guide ssDNA (guide ssDNA), at a suitable reaction temperature (such as about 90-98 degrees), the broken 5' nucleic acid fragments can be re-used by the PfAgo enzyme for the cutting of the complementary fluorescent reporter nucleic acid strand thereof. The results show that the method of the present invention can not only rapidly and high-throughput detect trace nucleic acid molecules, but also accurately provide detection results, thereby providing help for pathogen detection, genotyping, disease course monitoring, etc. On this basis, the present invention has been completed.

The Terms

As used herein, the terms "the detection system of the present invention" and "the nucleic acid detection system based on Argonaute protein" are used interchangeably and refer to the detection system described in the first aspect of the present invention.

As used herein, the terms "the detection method of the present invention" and "the nucleic acid detection method based on Argonaute protein" are used interchangeably and refer to the detection method described in the second aspect of the present invention.

As used herein, the terms "gene editing enzyme *Pyrococcus furiosus*", "nuclease *Pyrococcus furiosus*", and "PfAgo enzyme" are used interchangeably and refer to the enzyme described in the first aspect of the present invention.

As used herein, the term "secondary cleavage" means that in the detection method of the present invention, in the presence of the primary guide ssDNAs, the Ago enzyme of the present invention cuts the target nucleic acid sequence to form a new 5' phosphorylated nucleic acid sequence (secondary guide ssDNA); then, in the presence of the PfAgo enzyme, the secondary guide ssDNA continues to guide the PfAgo enzyme to cleave the fluorescent reporter nucleic acid complementary to the secondary guide ssDNA. This mode of specific cleavage for the target nucleic acid sequence first (first cleavage), and then specific cleavage for the fluorescent reporter nucleic acid (second cleavage), is defined as a "secondary cleavage". In the present invention, both the first cleavage and the second cleavage are specific.

Ago Enzyme

In the detection system and detection method of the present invention, a core component is a gene editing enzyme, such as Ago enzyme.

In the present invention, a preferred Ago enzyme is PfAgo enzyme, which is derived from the archaea *Pyrococcus furiosus*, with a gene length of 2313 bp and an amino acid sequence consisting of 770 amino acids.

The cleavage characteristics of PfAgo enzyme are: the enzyme can use 5' phosphorylated oligonucleotide as the guide ssDNA to guide the enzyme to precisely cleave the target nucleic acid sequence; and the cleavage site is located at the phosphodiester bond between the target nucleic acids (ssDNA) corresponding to the 10th and the 11th nucleotides of the guide ssDNA.

Generally, the preferred working temperature of PfAgo enzyme is 95±2 degrees.

Guide ssDNA Pair

In the detection system and detection method of the present invention, a core component is a guide ssDNA pair.

In the present invention, the preferred guide ssDNAs are all oligonucleotides with a length of 14-24 nt (e.g. 16 nt), and the first 5' nucleotides are all phosphorylated thymine (T).

As shown in FIG. 1, a pair of guide ssDNAs for the same DNA strand is binded to the target nucleic acid molecule, and the corresponding cleavage sites are marked by black arrows, and a blunt end is formed after the action of pfAgo enzyme.

Reporter Nucleic Acid Molecule

In the detection system and detection method of the present invention, a core component is a reporter nucleic acid carrying a reporter molecule.

The preferred reporter molecules are fluorescent molecules or fluorescent groups. A preferred reporter nucleic acid molecule is a nucleic acid molecule that carries a fluorescent group and a quenching group, respectively. For example, a fluorescent group (F) is labeled at the 5' end, and a quenching group (Q) is labeled at the 3' end. FIG. 2 shows a fluorescent reporter nucleic acid with a length of 17 nt, a fluorescent group (F) at the 5' end, and a quenching group (Q) at the 3' end.

In the present invention, the fluorescent reporter nucleic acid is determined according to the produced position of the secondary guide ssDNA; the target nucleic acid sequence is cleaved by the primary guide ssDNA to form a new 5' phosphorylated nucleic acid sequence, which is called the secondary guide ssDNA, and the fluorescent reporter nucleic acid covers the corresponding position of the secondary guide ssDNA (for example, 1st-16th bases).

Detection System

The present invention provides a detection system for detecting target nucleic acid molecules, which comprises:
 (a) a guide ssDNA pair;
 (b) a gene editing enzyme *Pyrococcus furiosus* Argonaute (Pf Ago); and
 (c) a fluorescent reporter nucleic acid, which has a fluorescent group and a quenching group;
wherein, the target nucleic acid molecule is target DNA.

Detection Method

The present invention also provides a nucleic acid detection method based on the gene editing enzyme *Pyrococcus furiosus* Argonaute (PfAgo).

In order to facilitate understanding, the inventor provides the principle of the detection method of the present invention. It should be understood that the protection scope of the present invention is not limited by the principle.

See FIG. 2 and FIG. 3. In the method of the present invention, based on the cleavage activity of the PfAgo enzyme, a series of guide ssDNAs can be designed according to the different target nucleic acid sequences. These guide ssDNAs target the nucleic acid to be detected and mediate the PfAgo enzyme to cleave the target fragment, to form a new secondary guide ssDNA. In the presence of the PfAgo enzyme, the secondary guide ssDNA continues to guide the PfAgo enzyme to cleave the fluorescent reporter nucleic acid complementary to the secondary guide ssDNA, so as to achieve the detection of the target nucleic acid.

In the present invention, according to the design requirements of the guide ssDNA, through a special design, the PfAgo enzyme can selectively cleave nucleic acid sequences that have differences in some sites, thereby realizing typing detection.

In the present invention, when used for distinguishing different types, when designing the guide ssDNA, the mutation sites corresponding to different types are placed in the 10th and 11th positions of the guide ssDNA. Due to the specificity of pfAgo enzyme selection, two consecutive point mutations can inhibit the cleavage activity, so as to achieve the detection of different types.

In a preferred embodiment, the present invention provides primers, guide ssDNAs, and fluorescent reporter nucleic acids for nucleic acid detection, for example, for the detection of the target gene PIK3CA E545K, or two types of HCV virus, JFH-1 2a and CON1-1b, respectively.

In the present invention, multiple target nucleic acids to be detected and guide ssDNAs can be added to the cleavage system of PfAgo enzyme at the same time, and the reporter nucleic acids with different fluorescent groups can be combined to achieve multiple detection of target nucleic acids.

The method of the present invention is very suitable for detecting trace amounts of nucleic acids. By combining PCR and a pair of guide ssDNAs with specific sequences, the present invention can detect target nucleic acids with a concentration as low as fM level.

In a preferred embodiment, the detection method of the present invention comprises the following steps:
  step 1: designing amplification primers, specific oligonucleotide guide ssDNAs and fluorescent reporter nucleic acids for different target nucleic acid sequences to be detected;
  step 2: collecting samples to be tested and extracting nucleic acid complexes containing the target sequence;
  step 3: using the obtained sample to be tested as the templates and adding different amplification primer pairs to perform a pre-amplification reaction;
  step 4: adding specific oligonucleotide guide ssDNAs, corresponding fluorescent reporter nucleic acids and PfAgo enzyme to the pre-amplification reaction system of step 3, to perform specific cleavage under the condition of continuous incubation at 95 degrees;
  step 5: performing quantitative real-time PCR analysis on the system of step 4;
  step 6: analyzing the image, and then adjusting the Start value, End value and threshold line of the Baseline to determine the result.

In the present invention, the Tm value of the amplification primer used in the amplification reaction is usually about 60±3 degrees, and the size of the amplified fragment is about 90-120 bp. Preferably, the amplification primer design should avoid the region to be detected.

Kit

The invention also provides a kit for the detection method of the invention.

Typically, the kit comprises:
  (a) a first container and a guide ssDNA located in the first container;
  (b) a second container and gene editing enzyme *Pyrococcus furiosus* Argonaute (PfAgo) located in the second container; and
  (c) a third container and a fluorescent reporter nucleic acid located in the third container.

In another preferred embodiment, the kit further comprises:
  (d) a fourth container and a buffer for gene editing enzyme digestion located in the fourth container.

In another preferred embodiment, the buffer for gene editing enzyme digestion comprises $MnCl_2$.

In another preferred embodiment, the kit further comprises:
  (f) a fifth container and a primer or a primer pair for amplifying target nucleic acid molecules located in the fifth container;
  (g) an optional sixth container and a polymerase for amplification reaction located in the sixth container; and
  (h) an optional seventh container and an amplification buffer for amplification reaction located in the seventh container.

Use

The present invention is particularly suitable for the detection of trace target nucleic acid molecules and multiple detections, and has a wide applicability.

In the present invention, the target nucleic acid molecule may be DNA or RNA. When the target nucleic acid molecule is RNA, it can be converted into DNA by reverse transcription and then detected.

In another preferred embodiment, the target nucleic acid molecules comprise target nucleic acid molecules derived from a species selected from the group consisting of: a plant, an animal, a microorganism, a virus, and a combination thereof.

In another preferred embodiment, the target DNA is a synthetic or a naturally occurring DNA.

In another preferred embodiment, the target DNA comprises a wild-type or a mutant DNA.

In terms of disease monitoring, the present invention can perform proactive management of diseases such as prediction and prevention, and achieve early detection and early treatment, or early prediction and early prevention. Due to the high detection sensitivity of the present invention, it is suitable for early diagnosis, thus for an antidote against the disease, saving the patient's treatment time and improving the treatment success rate. The invention reduces high medical cost and waste, and strives for a golden opportunity for treatment.

In terms of environmental monitoring, the present invention can accurately, conveniently and rapidly identify nucleic acid molecules in environmental pollutants and provide effective environmental detection data.

The main advantages of the present invention include:
1) The nucleic acid detection method based on the gene editing enzyme *Pyrococcus furiosus* Argonaute (PfAgo) of the present invention fully utilizes the cleavage characteristics of the enzyme, making it a highly specific detection method.
2) A variety of target nucleic acids to be detected with the corresponding primary guide ssDNAs and fluorescent reporter nucleic acids can be added to the reaction system of the present invention at the same time, to realize single-tube multiple detection.
3) The nucleic acid detection method of the present invention has high sensitivity, and the detection limit of nucleic acid is aM-fM level.
4) The nucleic acid detection method of the present invention has good specificity and can distinguish different types of nucleic acid sequences.
5) The nucleic acid detection method of the present invention has convenient operation, simple design and low price.

The invention is further illustrated below in conjunction with specific embodiments. It should be understood that the examples are not intended to limit the scope of the invention.

The experimental methods in the following examples which do not specify the specific conditions are usually in accordance with conventional conditions, such as conditions described in Sambrook et al., Molecular Cloning: Laboratory Manual (New York: Cold Spring Harbor Laboratory Press, 1989), or in accordance with the conditions recommended by the manufacturer. Unless otherwise stated, percentages and parts are by weight.

Sequence Information

The examples involved 3 groups of target gene enrichment and amplification oligonucleotide sequences, as shown in the following table.

| Group No. | Mutation site | PIK3CA E545K | CON1-1b | JFH-1 2a |
|---|---|---|---|---|
| 1 | Primer pair | SEQ ID NO: 2; SEQ ID NO: 3 | SEQ ID NO: 7; SEQ ID NO: 8 | SEQ ID NO: 12; SEQ ID NO: 13 |
| 2 | Guide ssDNA pair | SEQ ID NO: 4; SEQ ID NO: 5 | SEQ ID NO: 9; SEQ ID NO: 10 | SEQ ID NO: 14; SEQ ID NO: 15 |
| 3 | Fluorescent reporter nucleic acid | SEQ ID NO: 6 | SEQ ID NO: 11 | SEQ ID NO: 16 |

| SEQ ID NO: | Sequence (5'-3') |
|---|---|
| 1 | CTGTGACTCCATAGAAAATCTTTCTCCTGCTCAGTGATTTCAGAGAGAGGATCTCGTGTAGAAATTGCTTTGAGCTGTTCTTTGTCATTTTCCCT |
| 2 | CTGTGACTCCATAGAAAATCTTTCTCC |
| 3 | AGGGAAAATGACAAAGAACAGCTC |
| 4 | P-TTCTCCTGCTCAGTGA |
| 5 | P-TGAAATCACTGAGCAG |
| 6 | FAM-CTCGTCCTCTTTCTAAA-BHQ1 |
| 7 | ccggtgagtacaccggaattgc |
| 8 | gcagtcttgcgggggc |
| 9 | P-TGCCCAAATCTCCAGG |
| 10 | P-TATGCCTGGAGATTTG |
| 11 | FAM-AGTCTCGCGGGGGCACGCCCAAATCTCCAG-BHQ1 |
| 12 | ccggtgagtacaccggaattgc |
| 13 | gcagtcttgcgggggc |
| 14 | P-TGCCCAAATGGCCGGG |
| 15 | P-TATGCCCGGCCATTTG |
| 16 | VIC-TGGATAAACCCACTGTATGCCCGGCCATTT-BHQ1 |
| 17 | CYACWCGCAGTACMAAYWTRWCAHTATGTGC |
| 18 | TTGAAAAATAAAYTGYAAATCAWAYTCYTC |
| 19 | TTGTATGTGCAAGATG |
| 20 | TTGTATGTACCAGATT |
| 21 | TGGAGTACCAACGACA |
| 22 | TGCAGTATAGCAGACA |

Example 1

Preparation of Detection Reagents and the Detection Method

In this example, it provides a kit used in the nucleic acid detection method of the present invention based on the gene editing enzyme *Pyrococcus furiosus* Argonaute (PfAgo) and the usage method thereof.

1.1 Detection Reagents and Kits

In this example, the detection of the E545K mutation of the PIK3CA gene was taken as an example, and the corresponding specific target nucleic acid sequence is (SEQ ID NO: 1)
5'-CTGTGACTCCATAGAAAATCTTTCTCCTGCT

CAGTGATTTCAGAGAGAGGATCTCGTGTAGAAAT

TGCTTTGAGCTGTTCTTTGTCATTTTCCCT-3'.

Based on the method of the present invention, the corresponding detection reagents include:

(1) amplification primers F-primer and R-primer, wherein the specific sequences are as follows:

F-primer:
(SEQ ID NO: 2)
5'-CTGTGACTCCATAGAAAATCTTTCTCC-3'

R-primer:
(SEQ ID NO: 3)
5'-AGGGAAAATGACAAAGAACAGCTC-3'

(2) a specific guide ssDNA pair, comprising a sense strand guide ssDNA and an antisense strand guide ssDNA, wherein the specific sequences are as follows:

sense strand guide ssDNA:
(SEQ ID NO: 4)
5'P-TTCTCCTGCTCAGTGA-3' antisense strand guide ssDNA:
(SEQ ID NO: 5)
5'P-TGAAATCACTGAGCAG-3'

(3) a fluorescent reporter nucleic acid corresponding to the secondary guide ssDNA, wherein the specific sequence is as follows:

Fluorescent reporter nucleic acid: 5' FAM (fluorescent group)-CTCGTCCTCTTTCTAAA-BHQ1 (quenching group) 3' (SEQ ID NO: 6)

(4) an enzyme preparation for amplification reaction, such as AceQ qPCR Probe Master Mix (Vazyme)

(5) $MnCl_2$ solution: 10 mM $MnCl_2$ solution 1.2 Detection Method

The schematic diagram of the nucleic acid detection method based on the gene editing enzyme *Pyrococcus furiosus* Argonaute (PfAgo) of the present invention is shown in FIG. 3. The specific operation steps are as follows:

(1) The dry powders of the amplification primers F-primer and R-primer were dissolved in ultrapure water to prepare a 10 uM storage solution. The dry powders of sense strand guide ssDNA and antisense strand guide ssDNA were dissolved in ultrapure water to prepare a 100 uM storage solution. The fluorescent reporter nucleic acid dry powder was dissolved in ultrapure water to prepare a 10 uM storage solution.

(2) AceQ qPCR Probe Master Mix (2×) enzyme preparation, ultrapure water, and amplification primers were used for preparation of an amplification reaction premix (the final concentrations of amplification primers were 500 nM).
(3) The sample to be tested was added to the amplification reaction premix, and the reaction system was 20 uL.
(4) The amplification system was put into a PCR machine for amplification reaction (pre-denaturation at 95 degrees for 5 min, denaturation at 95 degrees for 15 sec, extension at 60 degrees for 15 sec, 30 cycles).
(5) After the amplification reaction was completed, PfAgo enzyme, $MnCl_2$, sense strand guide ssDNA, antisense strand guide ssDNA, and fluorescent reporter nucleic acid were added to the system in step (4), to make it a 25 uL reaction system (the final concentration of PfAgo enzyme was 200 nM, and the final concentration of $MnCl_2$ was 500 uM, and the final concentration of guide ssDNAs was 2 uM, and the final concentration of fluorescent reporter nucleic acid was 400 nM).
(6). The reaction system in step (5) was placed on a fluorescent quantitative PCR instrument for detection (incubation at 95 degrees for 30 min, and the fluorescent signal was detected once every minute).

Example 2

Detection of Different Concentrations of Nucleic Acids to be Tested

The specific target nucleic acids (SEQ ID NO: 1) was diluted according to the principle of 10-fold dilution method, into standard stock solutions of 200 pM, 20 pM, 2 pM, 200 fM, 20 fM, 2 fM and 0 fM. The nucleic acid standard stock solutions of different concentrations were added to the reaction system described in Example 1. The sample was added and the reaction was carried out according to the steps, and the fluorescent signal value at the wavelength of the corresponding fluorescent group was detected by fluorescent quantitative PCR.

Figure 4A:
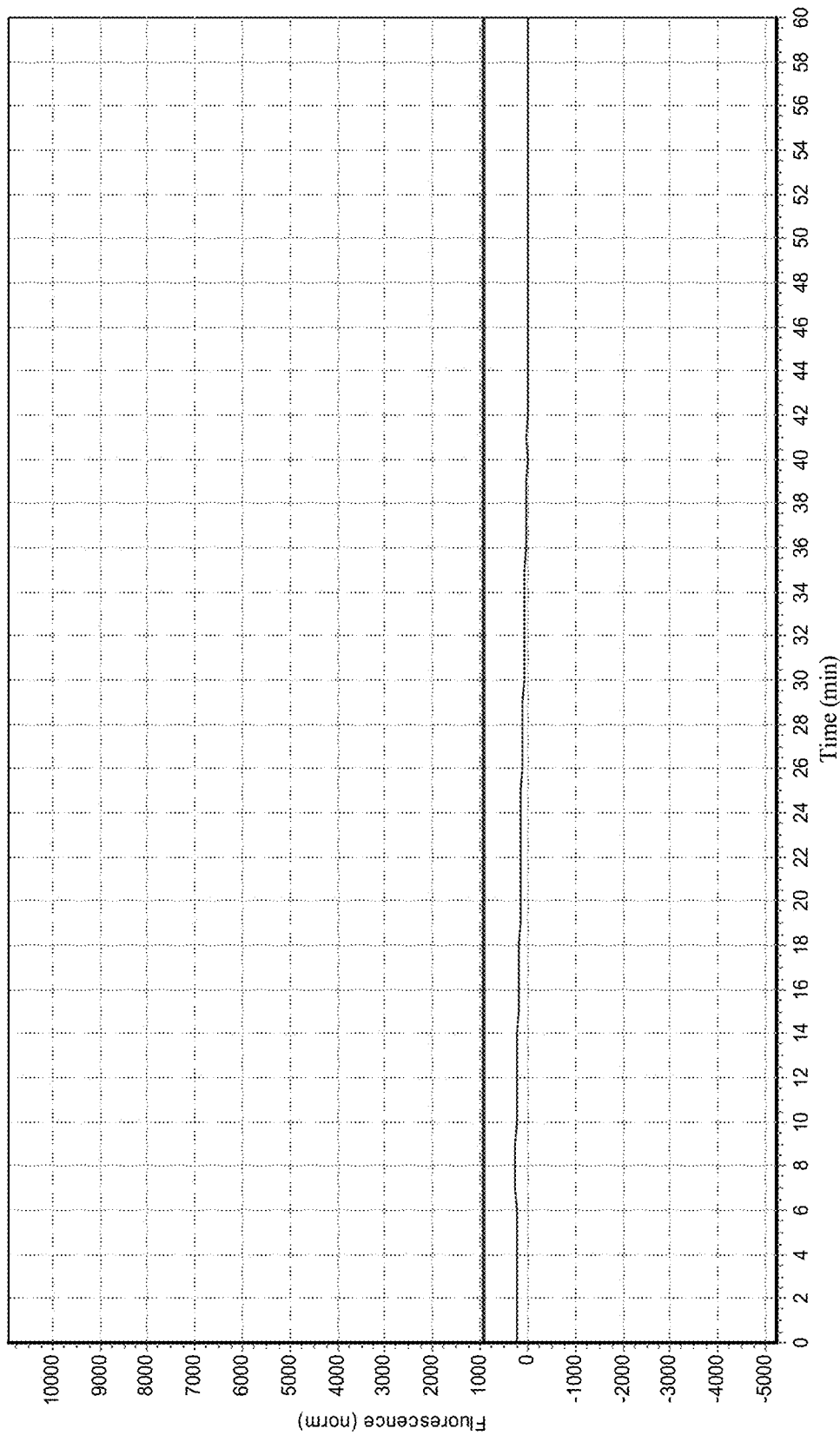
FIG. 4 shows the specificity and sensitivity of the nucleic acid detection system.
Figure 4B:
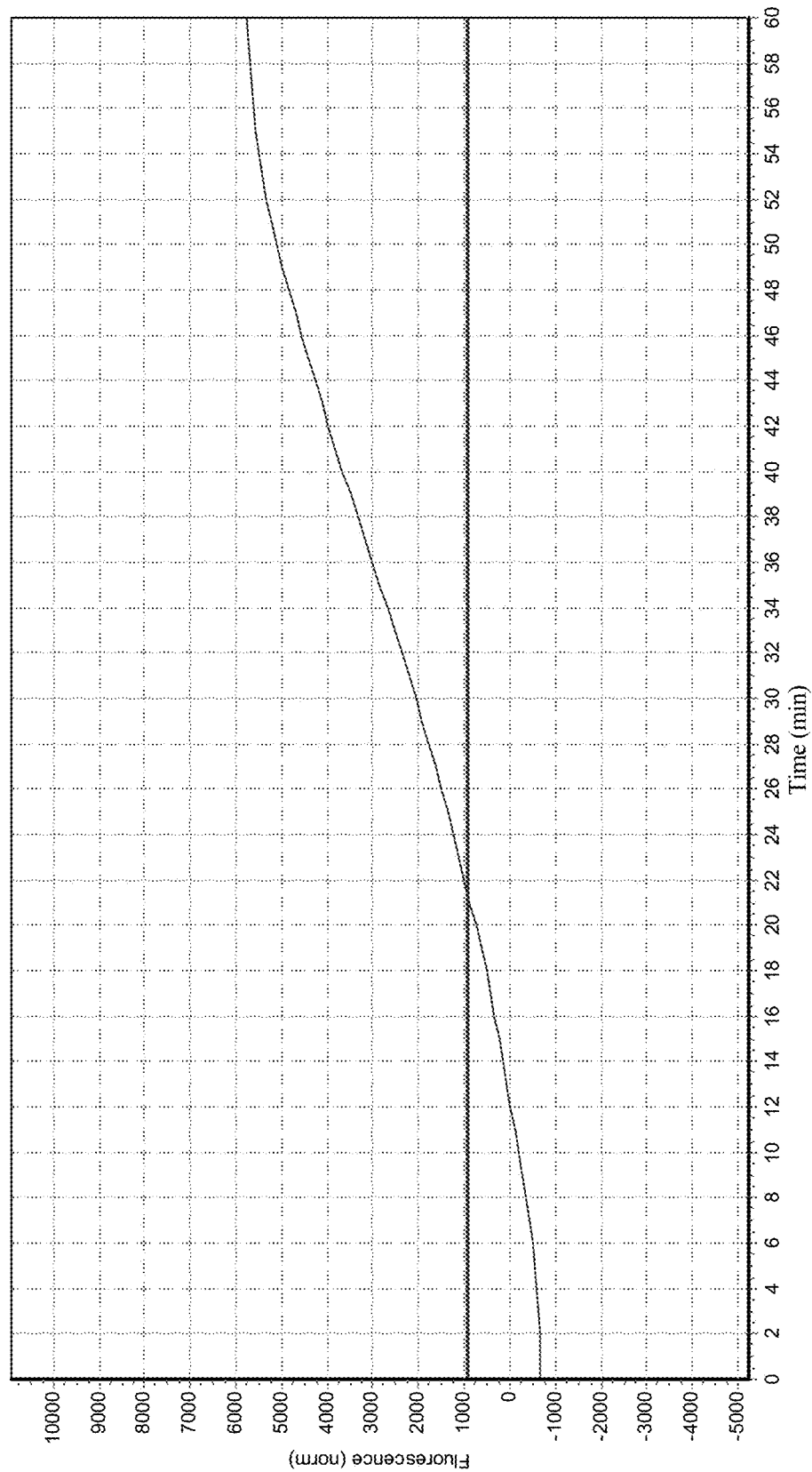
Figure 4C:
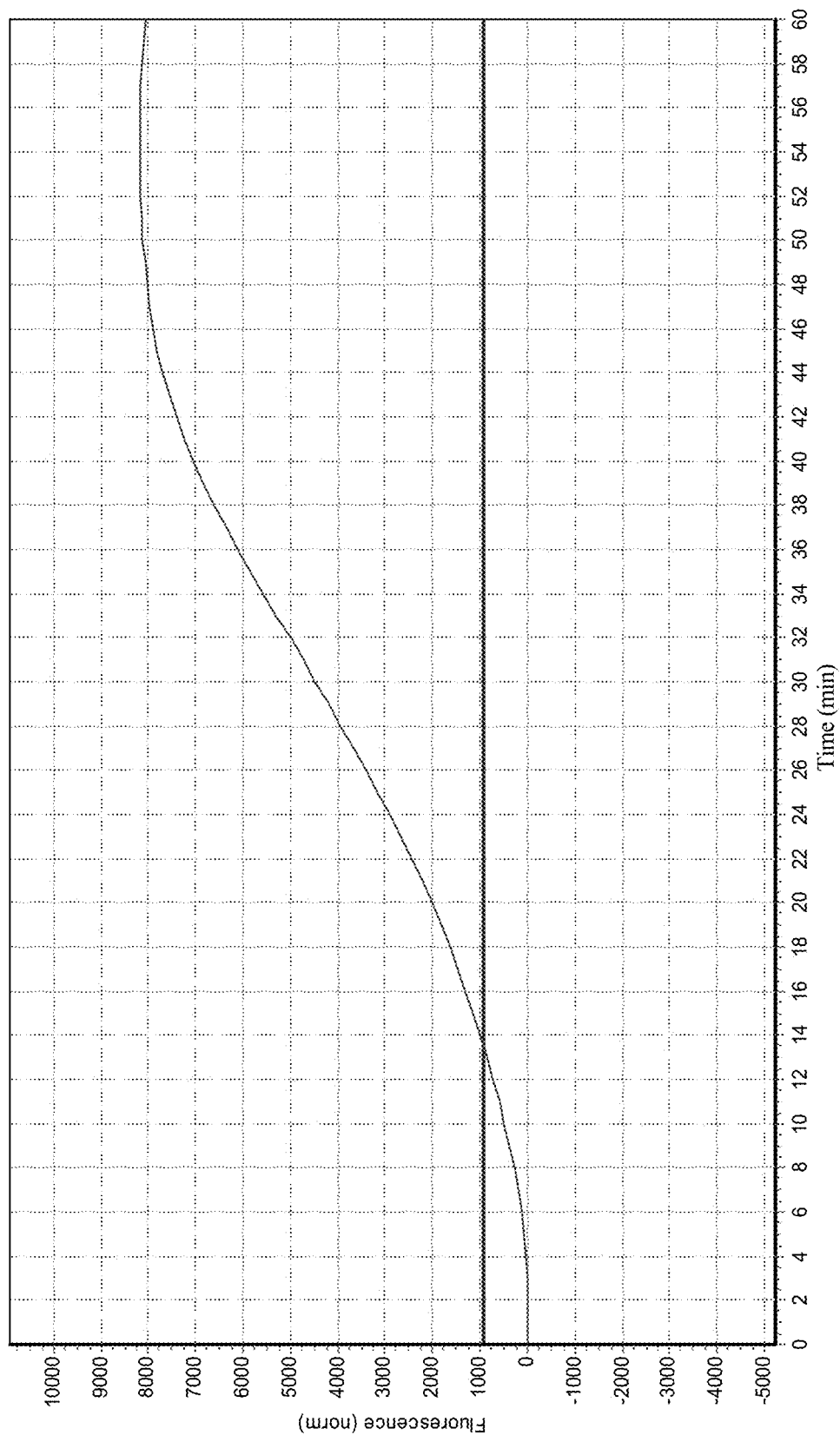
Figure 4D:
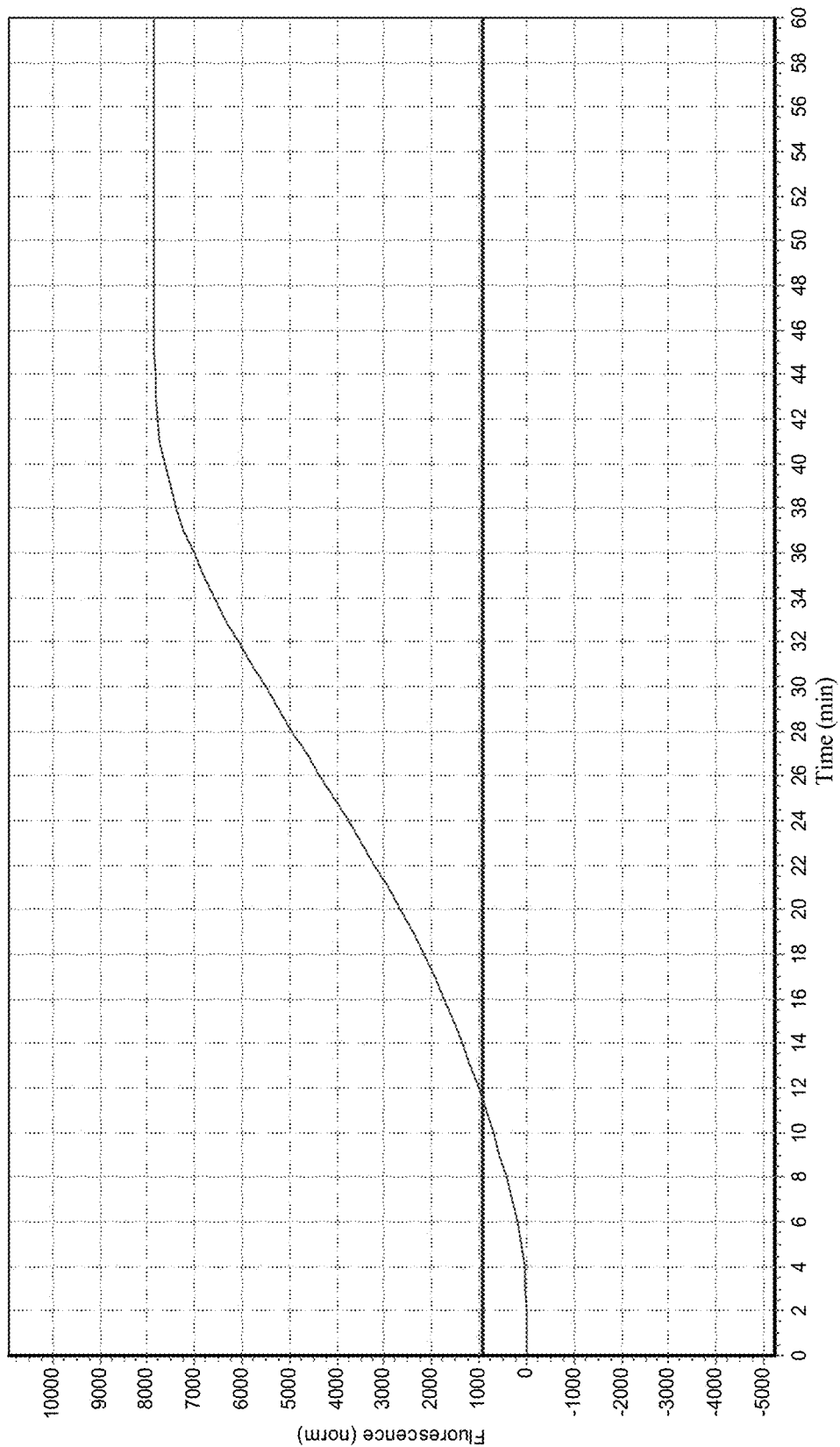
Figure 4E:
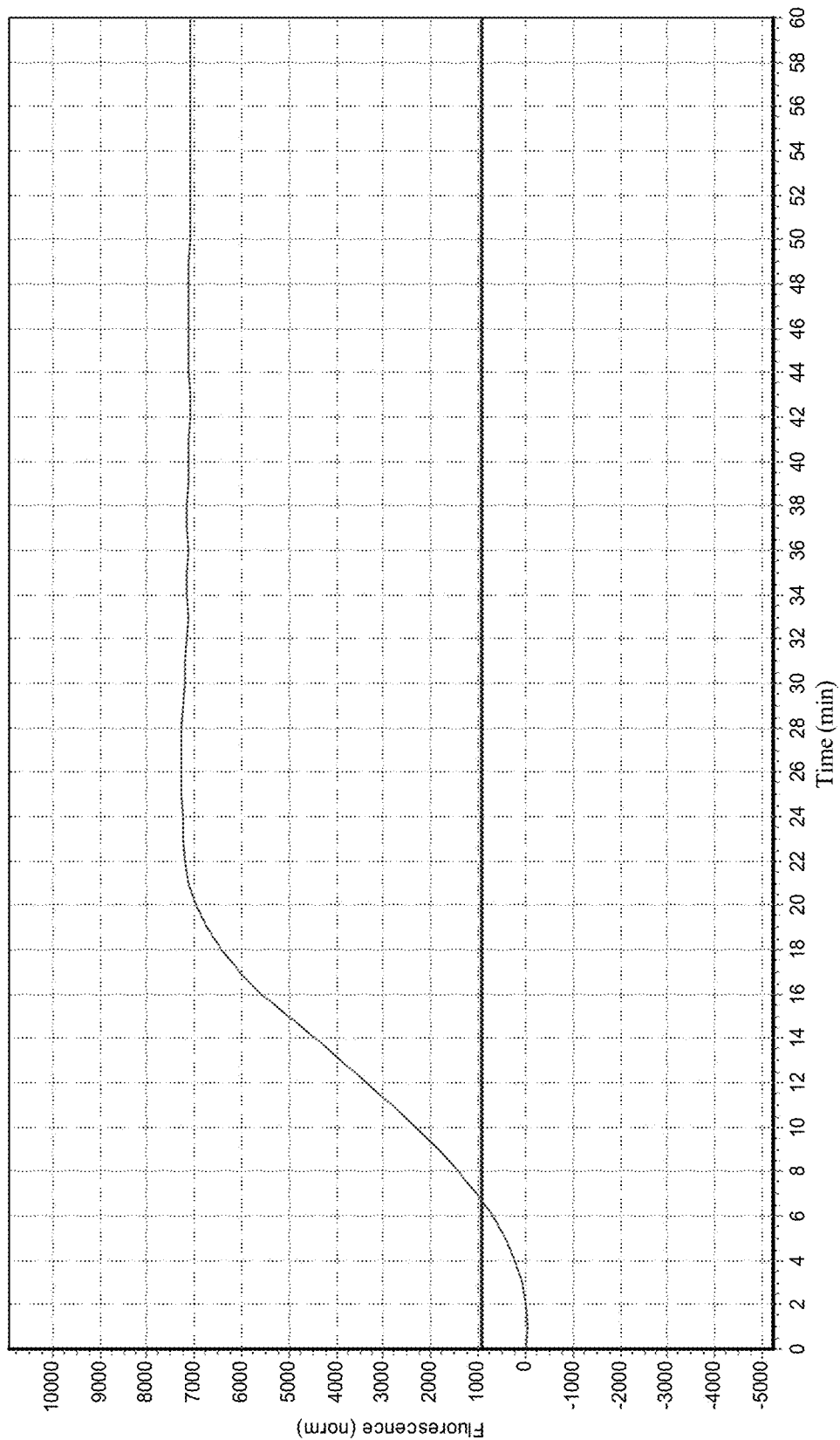
Figure 4F:
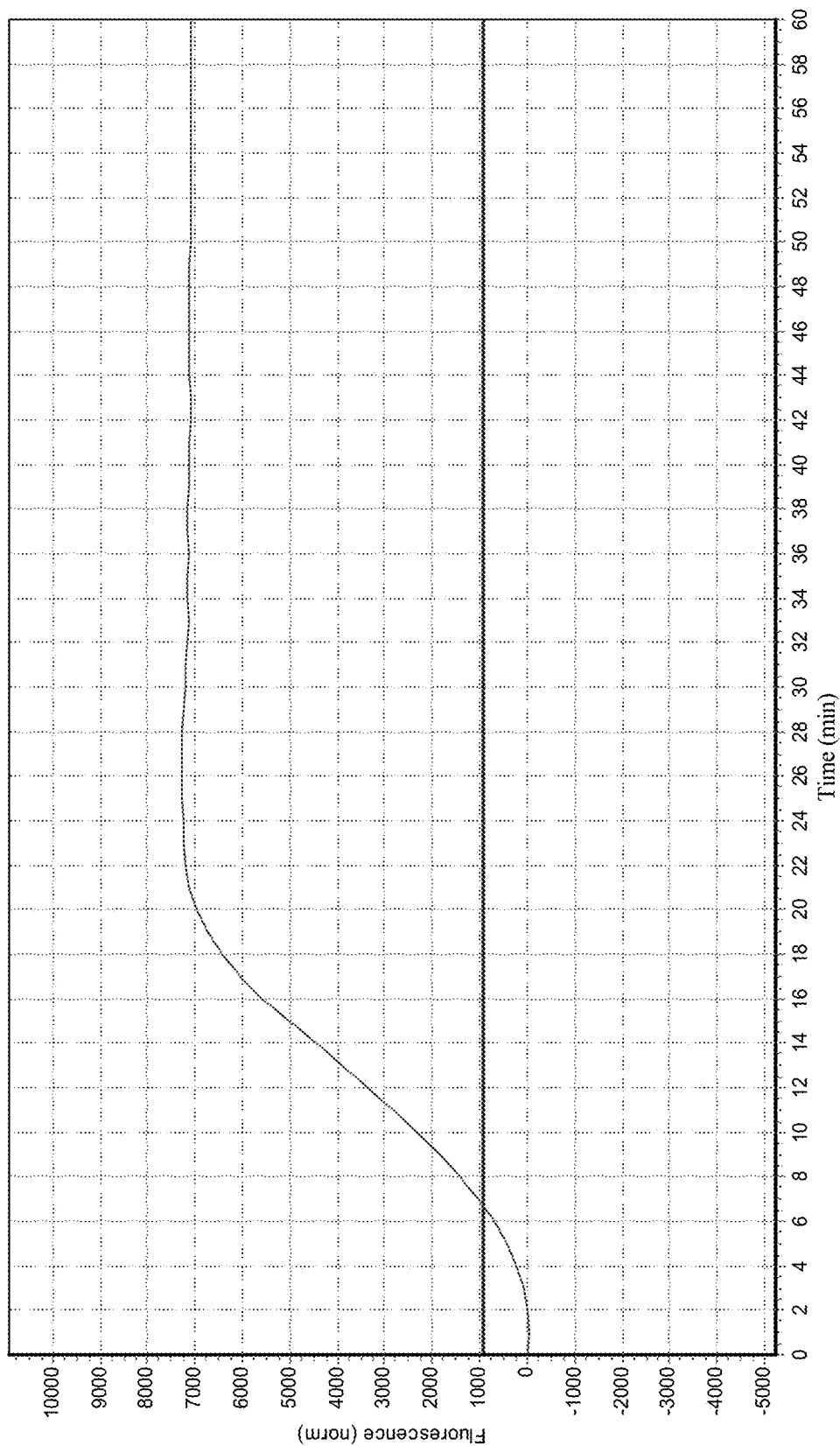
Figure 4G:
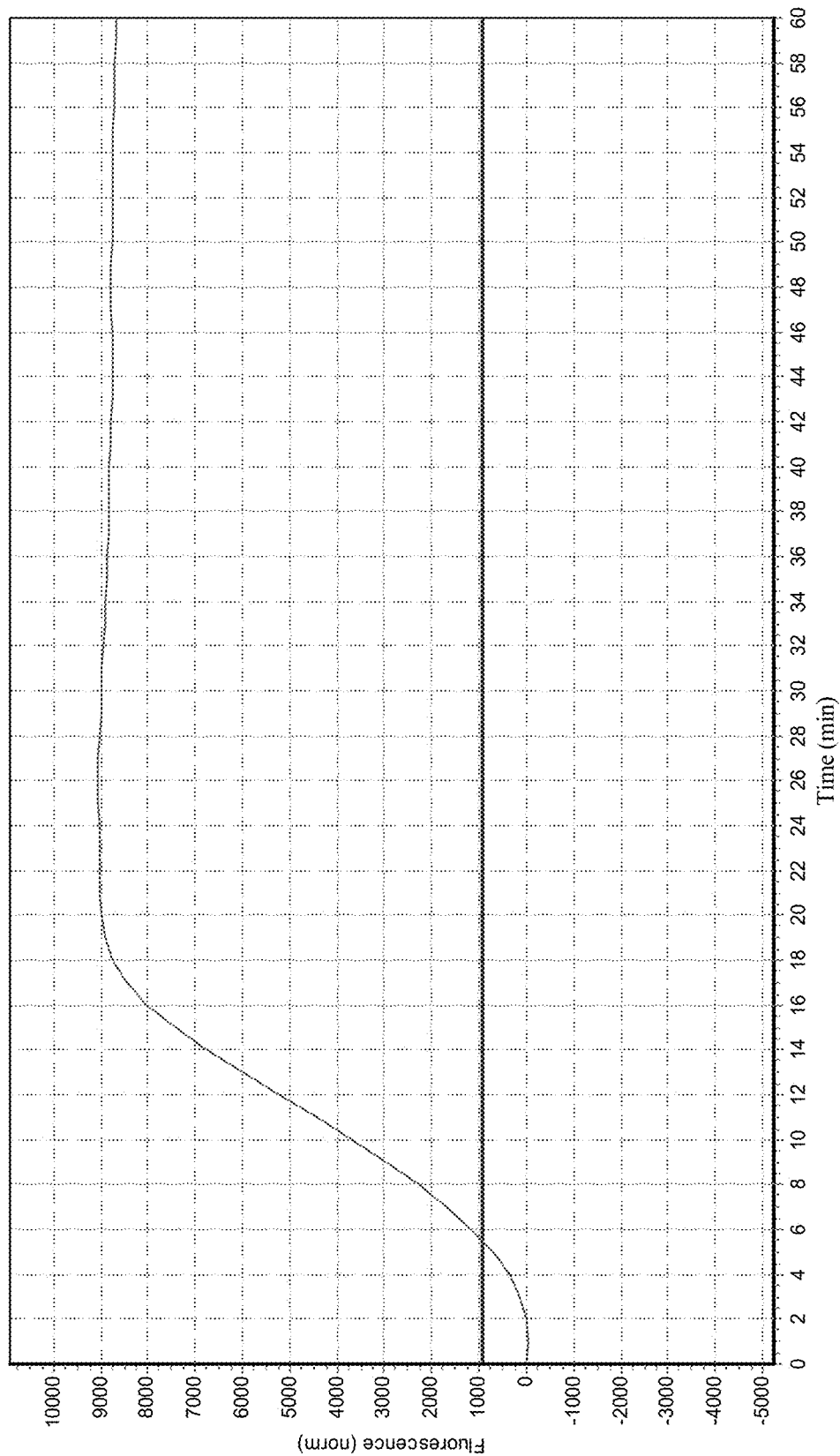
Figure 4H:
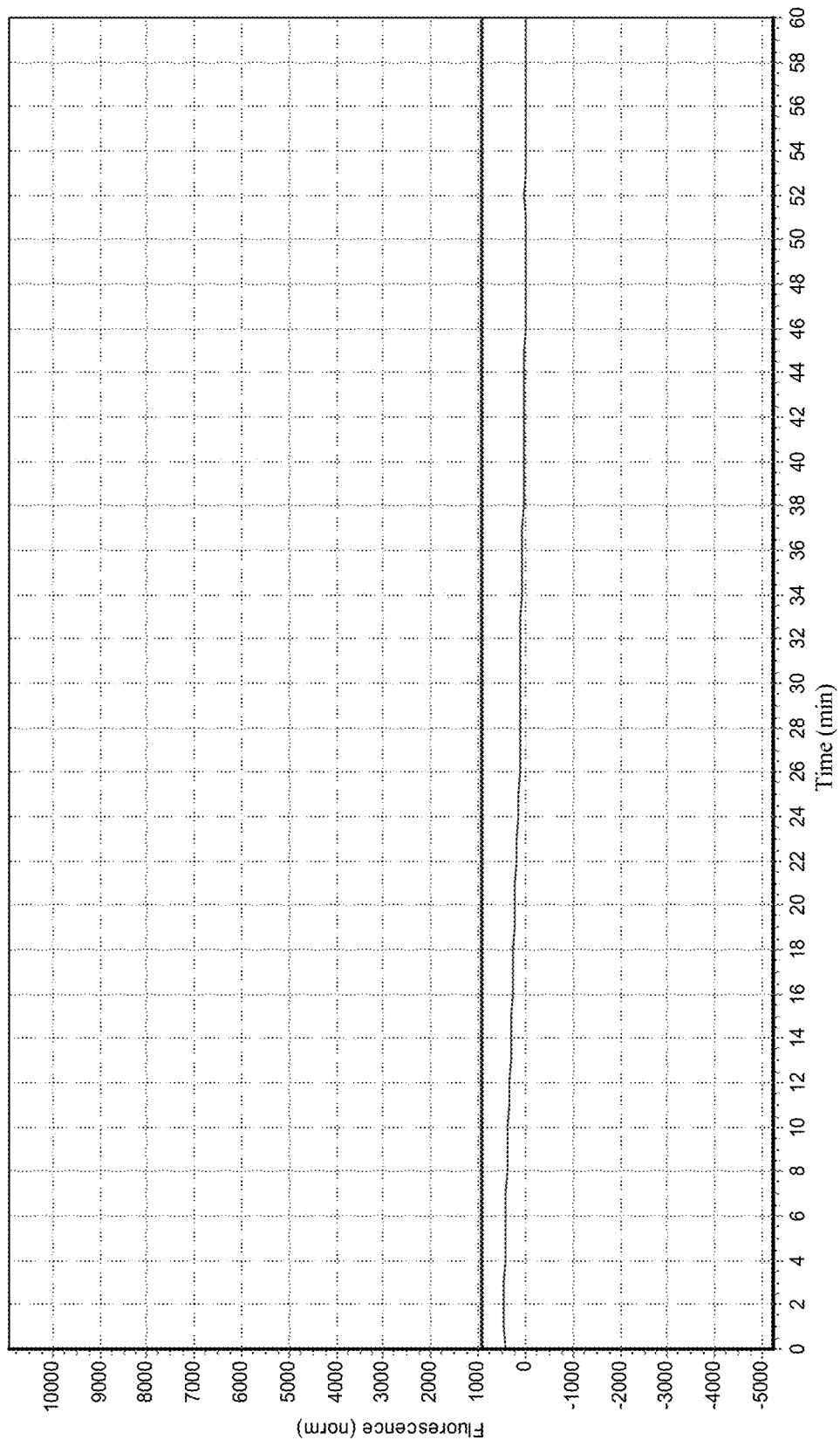
Figure 5A:
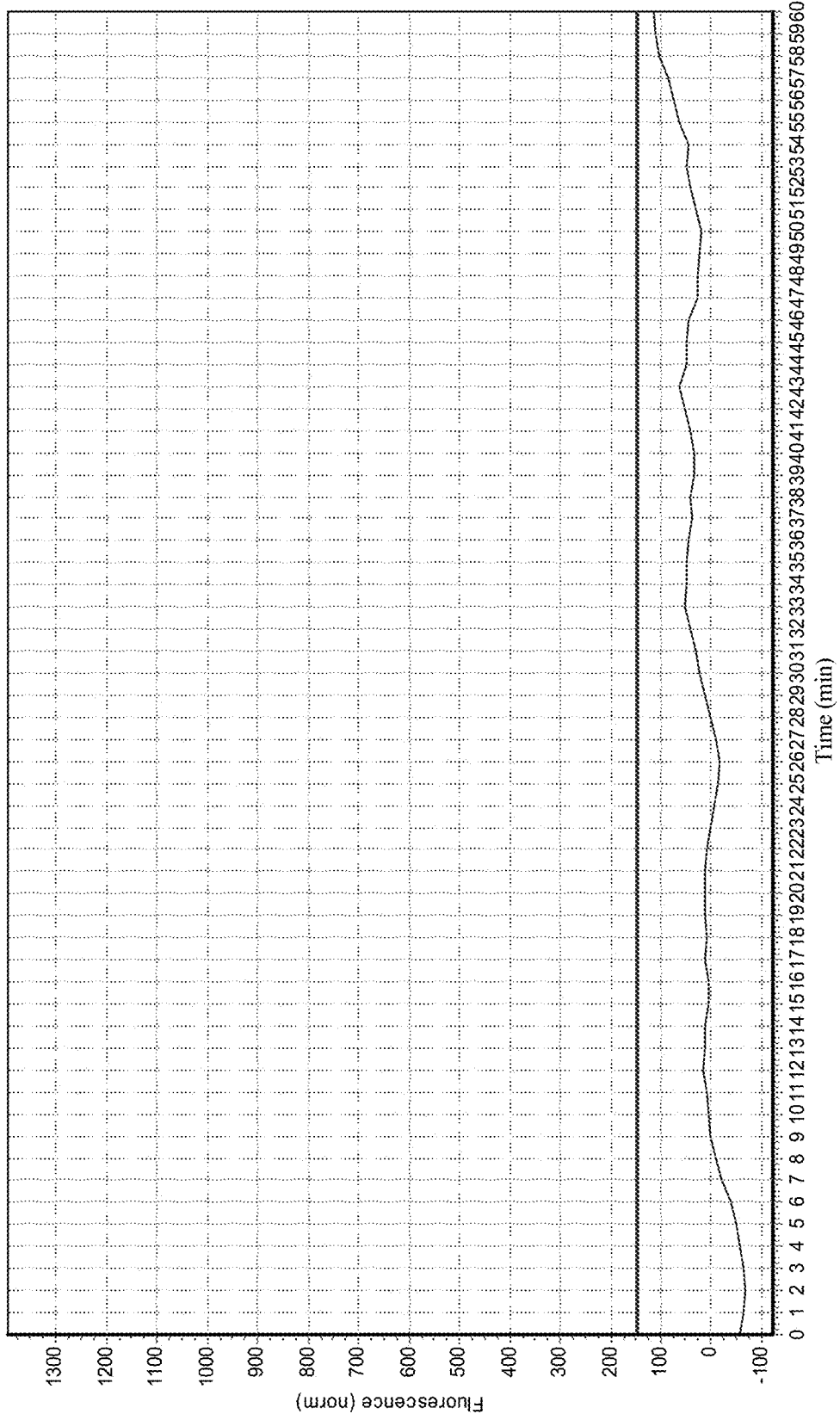
FIG. 5 shows the results of the multiplex experiment of the nucleic acid detection system in an example of the present invention. Wherein, in FIG. 5A, the CON1-1b-FAM reporter nucleic acid molecule (no template) was used.
in FIG. 5B, the CON1-1b-FAM reporter nucleic acid molecule (CON1-1b template) was used.
in FIG. 5C, the CON1-1b-FAM reporter nucleic acid molecule (JFH-1 2a template) was used.
in FIG. 5D, the JFH-1 2a-VIC reporter nucleic acid molecule (no template) was used.
in FIG. 5E, the JFH-1 2a-VIC reporter nucleic acid molecule (JFH-1 2a template) was used.
in FIG. 5F, the JFH-1 2a-VIC reporter nucleic acid molecule (CON1-1b template) was used.
Figure 5B:
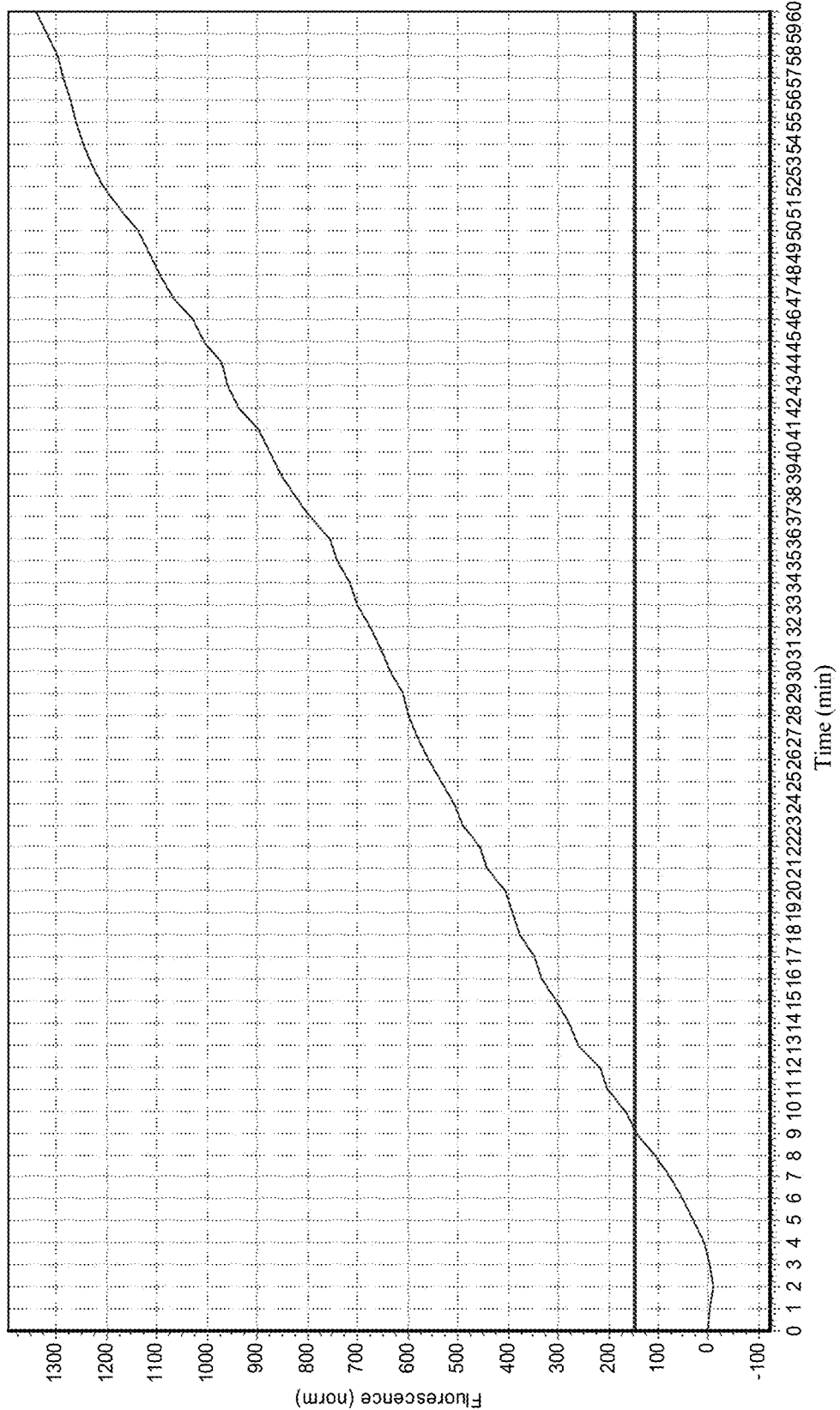
Figure 5C:
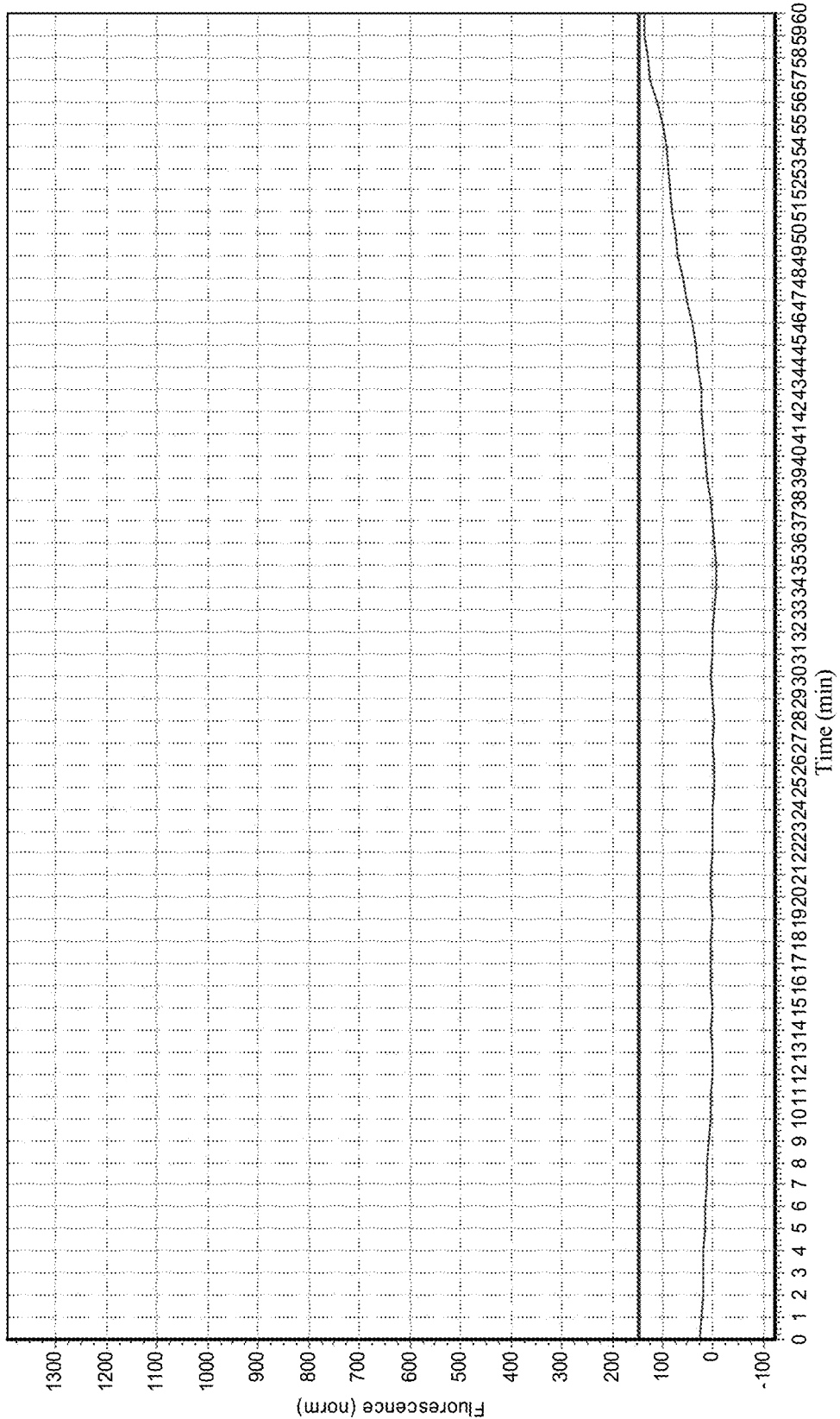
Figure 5D:
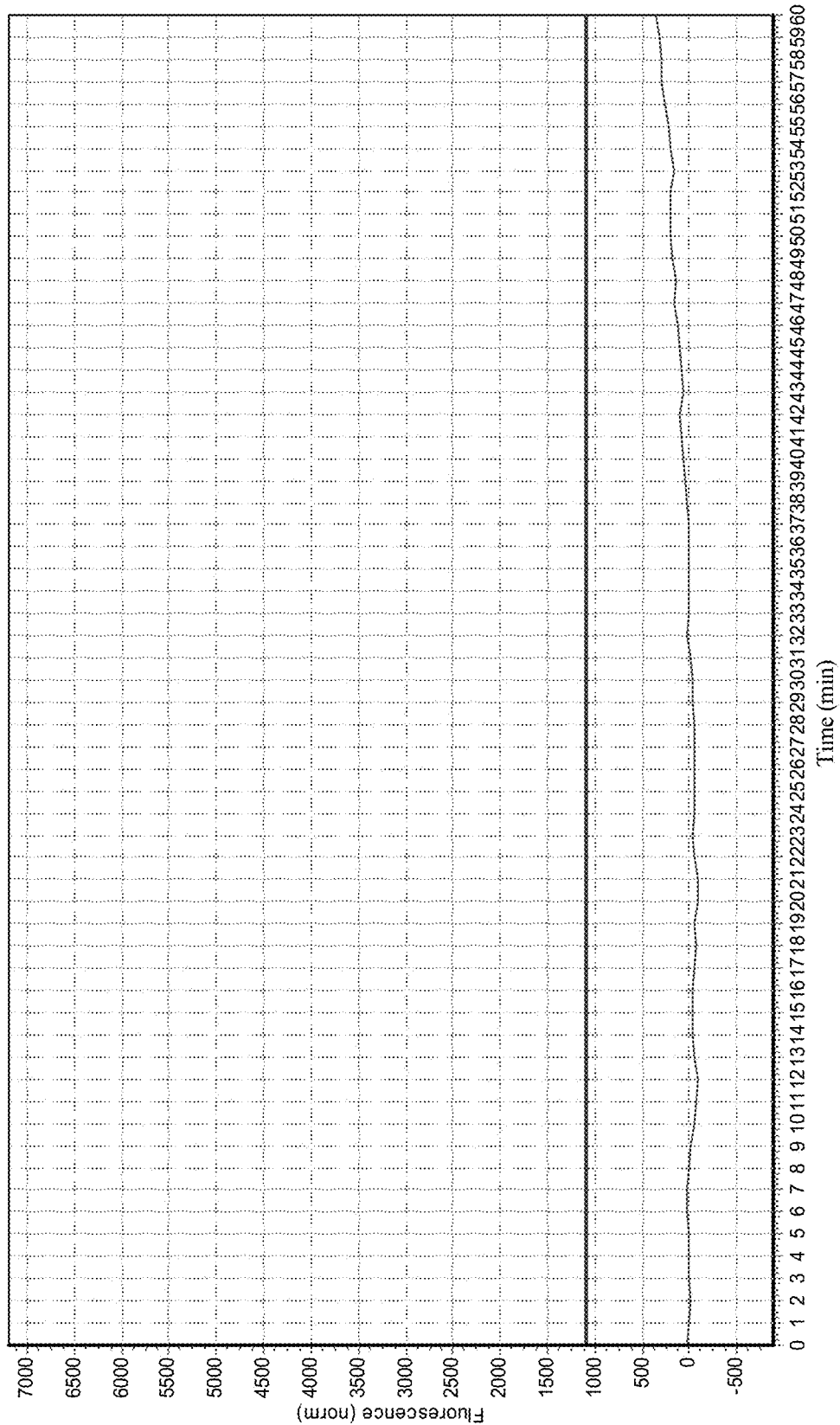
Figure 5E:
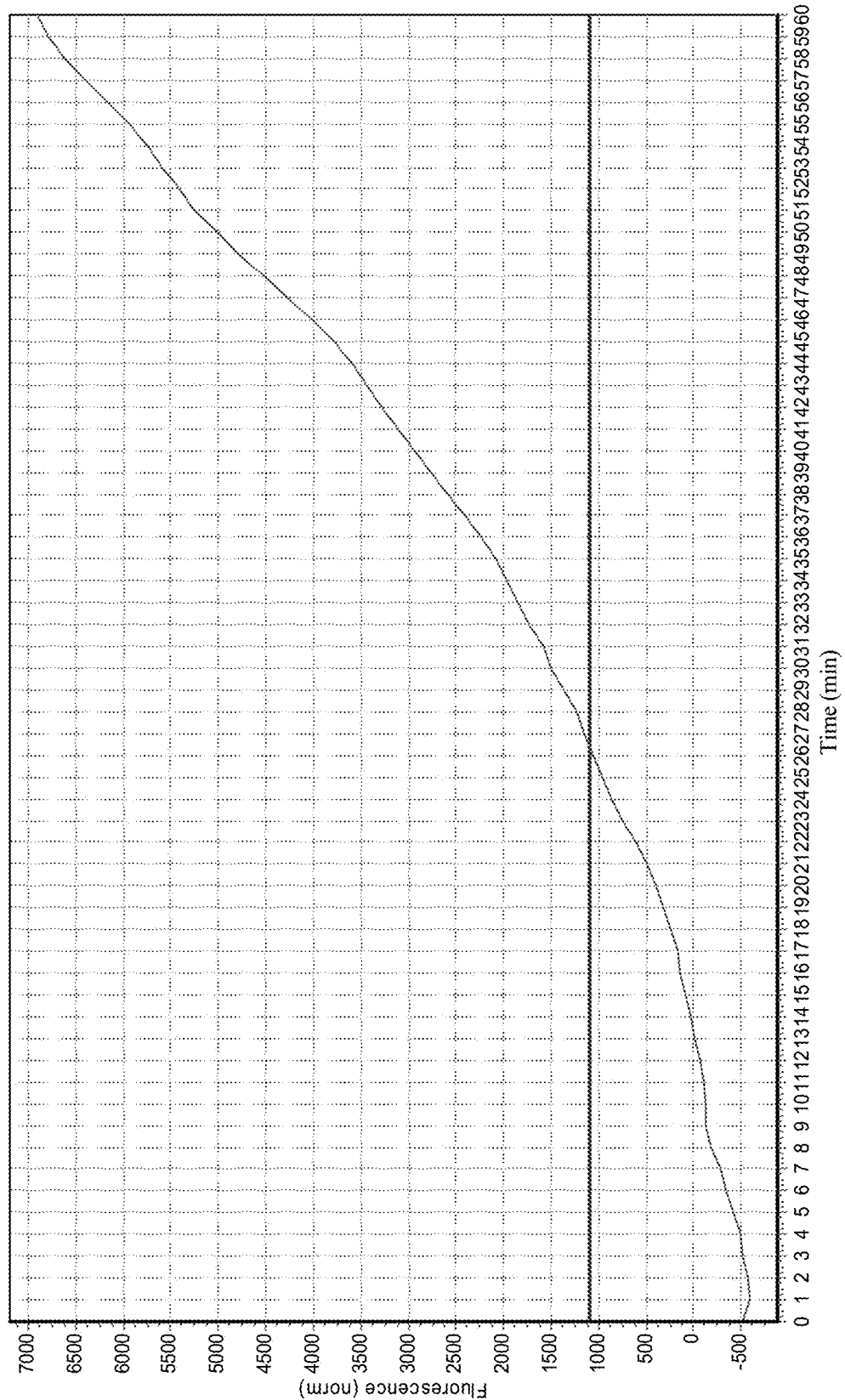
Figure 5F:
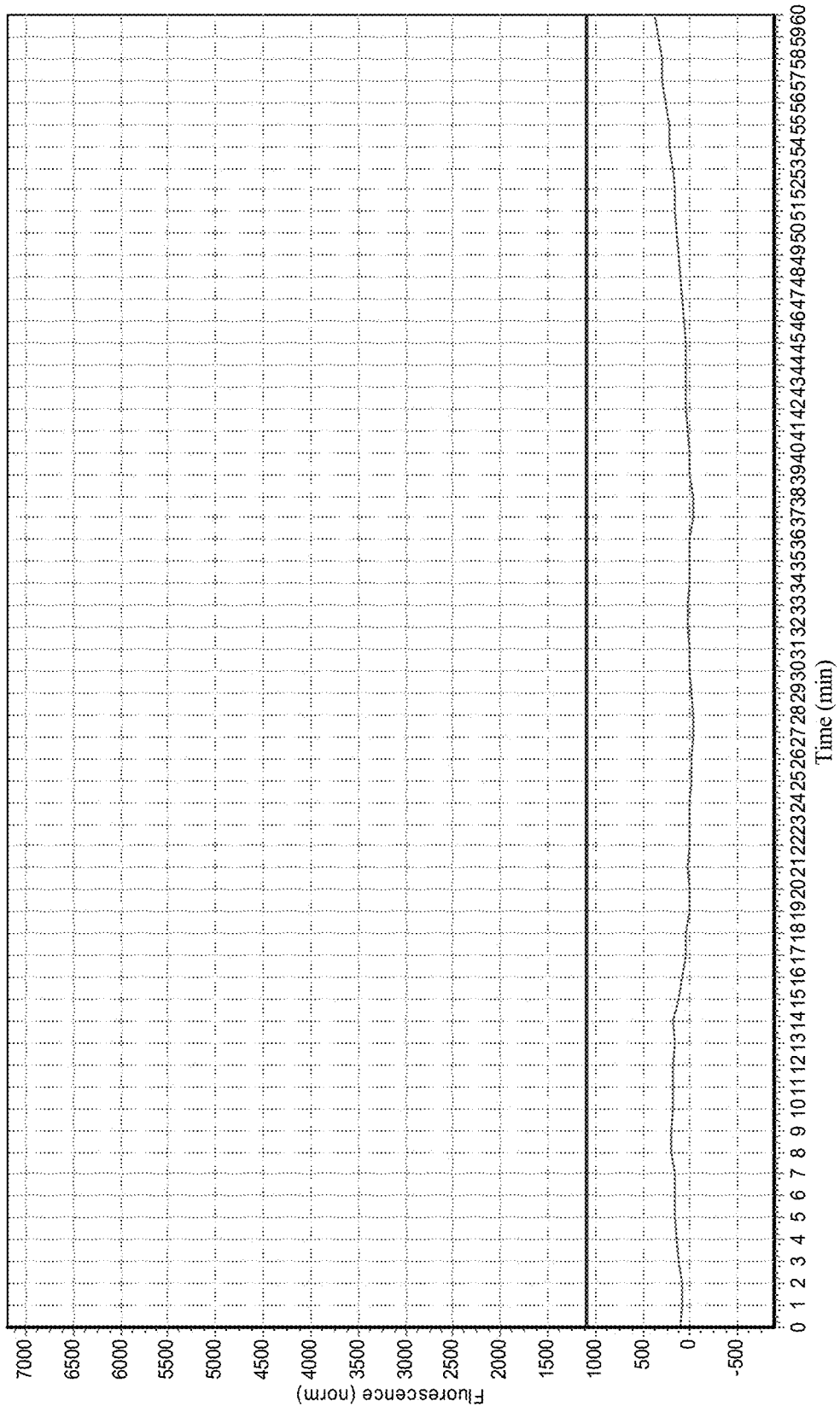

The results are shown in FIGS. 4A-4H. Wherein, the concentrations of the target nucleic acids in FIGS. 4A, 4B, 4C, 4D, 4E, 4F, 4G were 0 fM, 2 fM, 20 fM, 200 fM, 2 pM, 20 pM, 200 pM, and FIG. 4H shows the result of the non-target nucleic acids (20 ng was added to the system).

The non-target nucleic acid was the total DNA extracted from normal human serum. The results show that even if 20 ng of irrelevant non-target nucleic acids were added to the system, no positive results would be produced.

The results show that the method of the present invention can detect target nucleic acid molecules down to the fM level. In addition, for non-target nucleic acids, even if components of the detection system were added, positive signals would not be generated. Therefore, the method of the present invention has very high specificity.

Example 3

Specificity Test and Multiple Detection

Solutions of different types of target nucleic acids with a concentration of 200 pM were prepared, which were the two types of HCV viruses JFH-1 2a and CON1-1b, respectively.

It should be noted that the difference between these two types is that there are two consecutive positions different in the sequence.

Multiple mixed detection system was prepared. 2 pairs of specific amplification primers were added to the detection amplification system at the same time. And the target nucleic acids to be detected were added to the detection amplification system, according to the following 4 groups: (1) blank Control; (2) JFH-1 2a; (3) CON1-1b; (4) JFH-1 2a and CON1-1b. (FIG. 5 shows the specificity of the fluorescent reporter nucleic acids, which did not affect each other in one reaction system.)

After the amplification reaction was completed, PfAgo enzyme, $MnCl_2$, 2 groups of specific ssDNAs, 2 pairs of fluorescent reporter nucleic acids with different fluorescent groups (JFH-1 2a type corresponded VIC fluorescence, CON1-1b type corresponded FAM fluorescence) were added to the same reaction tube, and the detection was carried out according to the reaction steps in Example 1.

The results are shown in FIGS. 5A-5F. The results show that when the target nucleic acid to be detected was a blank control, no fluorescence signal value was generated; when the target nucleic acid to be detected was JFH-1 2a, only VIC fluorescence was generated; when the target nucleic acid to be detected was CON1-1b, only FAM fluorescence was generated; when the target nucleic acids to be detected were JFH-1 2a and CON1-1b, both FAM and VIC fluorescences were generated simultaneously. This shows that the nucleic acid detection method of the present invention can be used for multiple detection of a single tube.

Example 4

Four subtypes of human papillomavirus (HPV) were selected (HPV-6 (SEQ ID NO: 19), HPV-11 (SEQ ID NO: 20), HPV-16 (SEQ ID NO: 21), HPV-18 (SEQ ID NO: 22)) for multiple detection. Plasmids containing the above four genes were constructed for multiple experiments.

Four kinds of gDNAs, four kinds of reporter nucleic acids and a pair of degenerate amplification primers (SEQ ID NO: 17; SEQ ID NO: 18) required for multiple detection were designed.

After PCR amplification of the template DNAs of 16 kinds of combinations, multiple fluorescence detection was conducted.

After the amplification reaction was completed, PfAgo enzyme, $MnCl_2$, 4 kinds of specific ssDNAs, 4 kinds of fluorescent reporter nucleic acids with different fluorescent groups (HPV-6 type corresponded NED fluorescence, HPV-11 type corresponded ROX fluorescence, HPV-16 type corresponded FAM fluorescence, HPV-18 type corresponded JOE fluorescence) were added to the same reaction tube, and the detection was carried out according to the reaction steps in Example 1.

Figure 6:
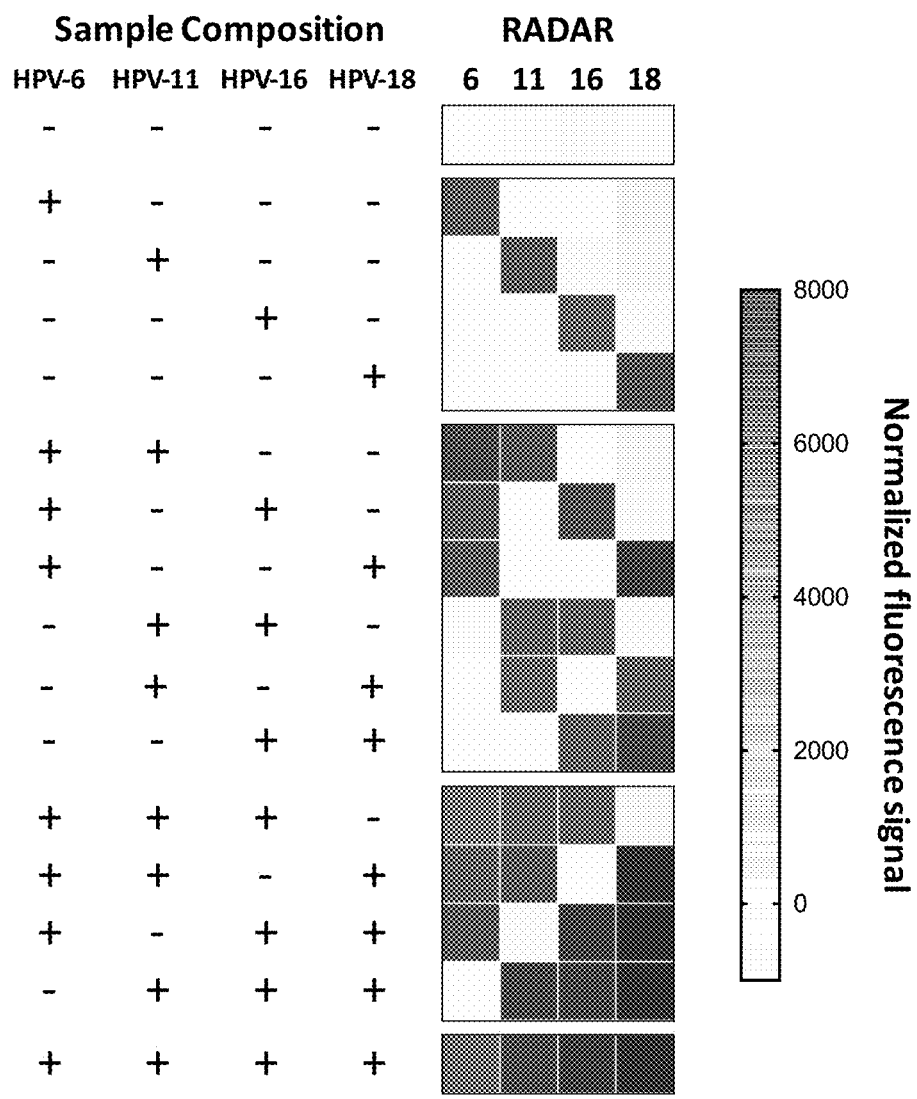
FIG. 6 shows the multiple detection result of different combinations of HPV, using plasmids as the samples.

The result is shown in FIG. 6. The results show that when the target nucleic acid to be detected was a blank control, no fluorescent signal value was generated; when the target nucleic acid to be detected was one or more of the HPV types, the corresponding fluorescent signal was collected and detected. This shows that the nucleic acid detection method of the present invention can achieve quadruple detection of a single tube.

The clinical HPV16/18 samples were used in this system for verification, and samples were added and reacted according to the above reaction system.

Figure 7:
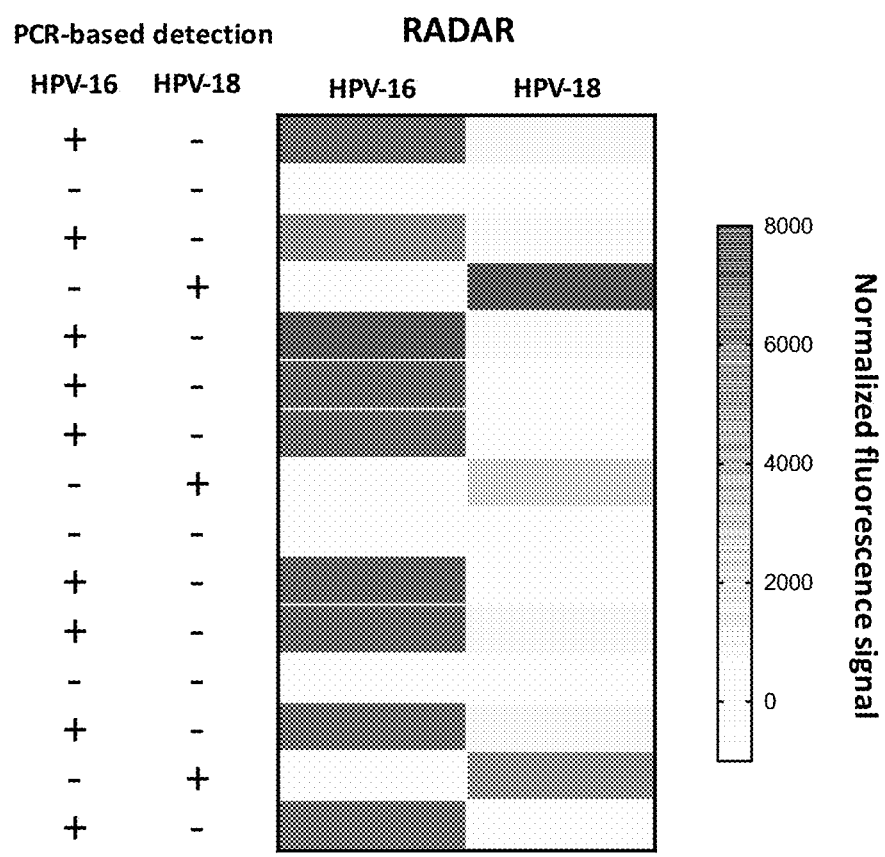
FIG. 7 shows the multiple detection result of high-risk subtype HPV16/HPV18, in the clinical samples.

The result is shown in FIG. 7. The results show that the detection system can be used for actual clinical detection, and has high sensitivity, high specificity, and rapid effect.

All publications mentioned herein are incorporated by reference as if each individual document was cited as a reference in the present application. It should be understood that, after reading the above teachings of the present invention, those skilled in the art can make various modifications and changes. These equivalent forms are also within the scope defined by the claims appended hereto.

The invention claimed is:

1. A detection system for detecting a target nucleic acid molecule, wherein the system comprises:
   (a) a guide ssDNA pair;
   (b) a gene editing enzyme *Pyrococcus furiosus* (Pf Ago); and
   (c) a fluorescent reporter nucleic acid, which has a fluorescent group and a quenching group;
   wherein:
      the target nucleic acid molecule is target DNA and is cleaved by the PfAgo enzyme to produce a secondary guide ssDNA,
      the sequences of the secondary guide ssDNA and the fluorescent reporter nucleic acid are complementary; and
      after complementary binding between the secondary guide ssDNA and the fluorescent reporter nucleic acid, the PfAgo enzyme is guided to cleave the fluorescent reporter nucleic acid, thereby generating a detectable signal.

2. The detection system of claim 1, wherein the length of the guide ssDNA is 14-60 nt, preferably 16-40 nt.

3. The detection system of claim 1, wherein the PfAgo enzyme is derived from the archaea *Pyrococcus furiosus*.

4. The detection system of claim 1, wherein the mutation sites corresponding to different types of the target nucleic acid molecules are at positions 10 and 11 of the guide SSDNA.

5. The detection system of claim 1, wherein the target nucleic acid molecules (or the amplification product thereof) are cleaved by the PfAgo enzyme to produce a secondary guide SSDNA.

6. The detection system of claim 1, wherein the detection system further comprises the target nucleic acid molecules to be detected, and the concentration of the target nucleic acid molecules to be detected in the detection system is 1 fM-200 pM.

7. The detection system of claim 1, the target DNA is selected from the group consisting of: single-stranded DNA (including cDNA), double-stranded DNA, and a combination thereof.

8. A kit for detecting target nucleic acid molecules, wherein the kit comprises:
   (i) the detection system according to claim 1 or reagents used for the preparation of the detection system; and
   (ii) instructions for use, which describe the method for detecting target nucleic acid molecules with the detection system.

9. A method for detecting the presence or absence of target nucleic acid molecules in a sample, comprising the steps of:
   (a) providing the detection system for detecting target nucleic acid molecules according to claim 1; and
   (b) reacting the detection system with the sample to be tested at a certain temperature, to form a first reaction solution;
   (c) performing a fluorescence detection on the first reaction solution, to obtain a fluorescence signal value;
   wherein, if the fluorescence signal value is detected in the first reaction solution, it indicates that there is target nucleic acid molecules in the sample; and if the fluorescence signal value is not detected in the first reaction solution, it indicates that there is no target nucleic acid molecule in the sample.

10. The detection system of claim 1, wherein the guide ssDNA is a 5'-phosphorylated single-stranded DNA molecule.

11. The detection system of claim 1, wherein the detection system further comprises primers for amplifying the target nucleic acid molecules.

12. The detection system of claim 6, wherein the molar ratio of the fluorescent reporter nucleic acid to the target nucleic acid molecules is $10^3:1$ to $10^8:1$, preferably $10^4:1$ to $10^7:1$.

13. The method of claim 9, wherein the sample to be detected comprises an unamplified sample and an amplified (or nucleic acid amplified) sample.

14. The method of claim 9, wherein the nucleic acid amplification method is selected from the group consisting of: PCR amplification, LAMP amplification, RPA amplification, ligase chain reaction, branched DNA amplification, NASBA, SDA, transcription-mediated amplification and rolling circle amplification.

* * * * *